United States Patent [19]

Entrekin

[11] Patent Number: 4,503,861
[45] Date of Patent: Mar. 12, 1985

[54] FETAL HEARTBEAT DOPPLER TRANSDUCER

[75] Inventor: Robert R. Entrekin, Bothell, Wash.
[73] Assignee: Biomedics, Inc., Isaaquah, Wash.
[21] Appl. No.: 500,061
[22] Filed: Jun. 1, 1983

Related U.S. Application Data

[63] Continuation of Ser. No. 483,985, Apr. 11, 1983.

[51] Int. Cl.³ ............................................. A61B 10/00
[52] U.S. Cl. ..................................... 128/661; 73/642
[58] Field of Search ................ 128/660, 661; 73/642, 73/644; 310/335, 336; 367/150

[56] References Cited

U.S. PATENT DOCUMENTS

| | | | |
|---|---|---|---|
| 3,168,659 | 2/1965 | Bayre et al. | 73/642 X |
| 3,387,604 | 6/1968 | Erikson | 73/642 X |
| 3,847,016 | 11/1974 | Ziedonis | 128/660 |
| 3,971,962 | 7/1976 | Green | 73/642 X |
| 4,184,094 | 1/1980 | Kopel | 310/355 |
| 4,205,686 | 6/1980 | Harris et al. | 73/644 X |
| 4,325,381 | 4/1982 | Glenn | 128/660 |
| 4,340,944 | 7/1982 | Dory | 73/642 X |
| 4,387,720 | 6/1983 | Miller | 128/660 |
| 4,391,281 | 7/1983 | Green | 73/644 X |

Primary Examiner—Kyle L. Howell
Assistant Examiner—Francis J. Jaworski
Attorney, Agent, or Firm—Cole, Jensen & Puntigam

[57] ABSTRACT

A doppler transducer which is particularly well adapted for use in fetal heartbeat measurements is comprised of a piston type transducer with a pair of lenses, which together provide both a divergent acoustic pattern and a flat surface for good acoustic coupling between the transducer and the mother's abdomen.

11 Claims, 2 Drawing Figures

FETAL HEARTBEAT DOPPLER TRANSDUCER

CROSS-REFERENCE TO RELATED APPLICATION

The present application is a continuation of co-pending application Ser. No. 483,985 filed Apr. 11, 1983.

BACKGROUND OF THE INVENTION

The present invention relates to a diagnostic ultrasound device. In particular, the invention relates to a doppler ultrasound transducer of the type used for measuring fetal heartbeats.

There are a number of transducers which are used in conjunction with doppler shift ultrasound equipment for measuring fetal heartbeat. A problem with transducer assemblies of the type which were used heretofore is that they have a limited acceptance angle. Accordingly, it was frequently necessary to reposition such transducers on the mother's abdomen as the baby moved during labor. In addition, many of the "daisy" type transducers which were known before had sensitivity problems in the near range.

Accordingly, it would be highly desirable to have a doppler transducer with a substantially increased acceptance angle and better near range sensitivity in order to reduce the amount of repositioning required, while maintaining an acceptable monitoring performance.

SUMMARY OF THE INVENTION

In accordance with the present invention, an doppler ultrasound transducer particularly well adapted for use in measuring fetal heartbeat is provided. The transducer is comprised of a substantially cylindrical, piston type piezoelectric element. There is a quarter-wave acoustic matching layer on the piezoelectric element, and a first acoustic lens on the acoustic matching layer. The first lens is convex, and it is designed to diverge sound. A second acoustic lens is formed on the first acoustic lens. The second lens is convex and is also designed to diverge sound. The second lens has a substantially flat surface on the side remote from the first lens. Thus, the combination of the first lens and the second lens provides a divergent lens. The material for each of the lenses is selected to have a desired acoustic velocity, and the degree of curvature of the interface between the two lenses is selected in order to provide any desired acceptance angle, yet the transducer can still be made to have a substantially flat surface for patient interface.

DESCRIPTION OF THE PREFERRED EMBODIMENT

Figure 2:
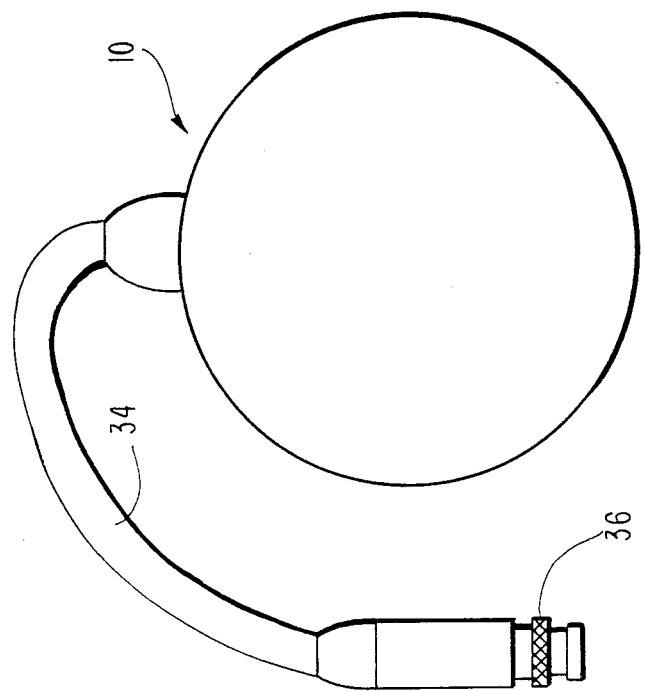
FIG. 2 is a top plan view of the device of FIG. 1.
Figure 1:
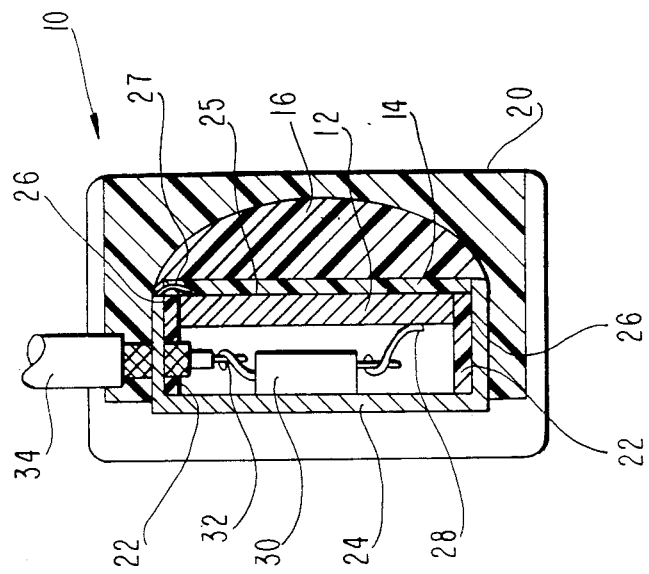
FIG. 1 is a cross-sectional pictorial view of the preferred embodiment of the invention.

Referring generally to FIGS. 1 and 2, the doppler transducer 10 of the present invention is shown. The transducer is preferrably comprised of a flat, circular disk of lead-zirconate-titanate ceramic (hereinafter called "PZT") 12, the material of which ultrasound transducers are typically made, although any other suitable piezoelectric material could be used without departing from the invention.

In the first embodiment of the invention, there is a quarter wave matching layer 14 of a material having a velocity and thickness such that it is one-quarter wavelength thick at the operating frequency of the PZT disk 12. The acoustic impedance of the matching layer 14 should be intermediate the PZT acoustic impedance and the acoustic impedance of human body tissue. Typically, a filled epoxy is used for the quarter wave layer 14. On the quarter wave layer 14, a spherical lens 16, constructed of a second filled epoxy, such as 3M brand XP-241-34 syntactic foam, is formed. The velocity of the lens 16 must be substantially higher than the velocity of sound in the human body, and its acoustic impedance should closely match that of the human body. The lens 16 diverges the sound waves from the piezoelectric element 12. A second lens element 18, comprised in the present invention of a material whose velocity is substantially lower and whose acoustic impedance closely matches human body is cast in place on the first lens 16. In the preferred embodiment of the invention, a silicone rubber material, such as Sylgard 170 brand material manufactured by Dow Corning Inc. of Midland, Mich., is used for the second lens 18. The combination of the convex first lens 16 and the concave second lens 18 provides a divergent lens, yet leaves a flat surface 20 for patient interface.

The transducer 10 further comprises a ring 22 formed of an insulating material such as Delrin. The ring 22 is used to provide an air backing which allows efficient transfer of acoustic energy from the transducer element 12 into the human body. The Delrin ring 22 is enclosed by a metal case 24, comprised of brass in the preferred embodiment of the invention. The brass case 24 is electrically connected to the front surface 25 of the piezoelectric element 12 via a soldered wire 27 in order to provide a first electrical connection thereto. A second electrical connection 28 is made between the back of the piezoelectric element 12 and an inductor 30. The inductor 30 is also connected to the center wire 32 of a coaxial cable 34. The ground 36 of the coaxial cable 34 is connected to the piezoelectric element 12 via the brass case 24. The inductor 30 is selected to tune out the capacitive impedance of the piezoelectric element 12 at the frequency of operation. The coaxial cable 34 is connected to a fetal monitor by means of a BNC connector 36.

A fetal monitor built in accordance with the preferred embodiment of the invention will be either of the pulsed type or of the continuous wave type. If the fetal monitor uses pulsed doppler, then only one transducer 10 is required. If the fetal monitor uses continuous wave doppler then it normally consists of two separate transducers 10. In that event, one of the transducers 10 is used for transmission and the other transducer 10 is used for reception. Each transducer 10 has a one-way acceptance angle of approximately 45 degrees. The transducers 10 are separate, so that their relative positions on the abdomen can be easily changed in order to evaluate the optimum configurations for a particular individual. It has been found that a fetal monitor using two such transducers 10 manufactured in accordance with the present invention is approximately 10 to 100 times more sensitive to targets which are located in the first 5 to 10 centimeters of depth below the mother's abdomen than when transducers of the prior art are used.

There are various other advantages associated with the using the transducer 10 of the present invention. In particular, the use of two lenses 16, 18 enables the designer to obtain any arbitrary flatness or curvature for fitting to the mother's abdomen while providing an arbitrarily large acceptance angle. In addition, the use of two lenses 16, 18 insures that the size of the contact area with the body can be adjusted to keep power density below any desired arbitrary figure.

I claim:

1. A transducer for a doppler ultrasound fetal monitor, comprising:
   a. A substantially cylindrical, piston-type piezoelectric element;
   b. An acoustic matching layer on said piezoelectric element;
   c. A first acoustic lens on said acoustic matching layer;
   d. A second acoustic lens on said first acoustic lens, wherein said first acoustic lens is convex, and said second acoustic lens is concave in the direction of said first acoustic lens and substantially flat in the direction of the patient, the curvature of the interface between said first and second acoustic lenses and the acoustic velocities of said first and second acoustic lenses, respectively, being selected so that the combination of said first and second acoustic lenses provide a divergent lens of selected acceptance angle with a substantially flat surface for patient interface.

2. The transducer of claim 1 wherein said piezoelectric element is comprised of PZT.

3. The transducer of claim 2 wherein said acoustic matching layer on said piezoelectric element is a quarter wave matching layer.

4. The transducer of claim 3 wherein said acoustic matching layer is comprised of a filled epoxy.

5. The transducer of claim 4 wherein said first acoustic lens is a spherical lens.

6. The transducer of claim 5 wherein said first acoustic lens is comprised of a material whose acoustic velocity is substantially higher than the velocity of sound in the human body and whose acoustic impedance closely matches that of the human body.

7. The transducer of claim 6 wherein said first acoustic lens is comprised of a filled epoxy.

8. The transducer of claim 7 wherein said filled epoxy comprising said first acoustic lens is comprised of 3M brand syntactic foam.

9. The transducer of claim 8 wherein said second acoustic lens is comprised of a material whose acoustic velocity is substantially lower than the velocity of sound in the human body and whose acoustic impedance closely matches that of the human body.

10. The transducer of claim 9 wherein said second acoustic lens is comprised of a silicone rubber material.

11. The transducer of claim 10 wherein said second acoustic lens is comprised of Sylgard 170 brand silicone rubber.

* * * * *